United States Patent [19]

Ishikawa et al.

[11] 4,138,491
[45] Feb. 6, 1979

[54] METHOD FOR TREATING DIABETES

[75] Inventors: Fumiyoshi Ishikawa; Akira Kosasayama; Yoshifumi Watanabe; Yasushi Abiko; Kin-ya Kameda; Shin-etu Ono, all of Tokyo, Japan

[73] Assignee: Daiichi Seiyaku Co., Ltd., Tokyo, Japan

[21] Appl. No.: 809,814

[22] Filed: Jun. 24, 1977

[30] Foreign Application Priority Data

Jun. 24, 1976 [JP] Japan ................... 51-74668

[51] Int. Cl.² .................. A61K 31/44; A61K 31/415
[52] U.S. Cl. ........................... 424/263; 424/273 R
[58] Field of Search .......................... 424/263

[56] References Cited
U.S. PATENT DOCUMENTS

| | | | |
|---|---|---|---|
| 2,604,473 | 7/1952 | Sperber et al. | 260/293.68 |
| 2,676,964 | 4/1954 | Sperber et al. | 260/309.6 |

OTHER PUBLICATIONS

*Chem. Abstr.* vol. 72 (1970) 3179oy.
*J. Chem. Soc.* (1950), pp. 188–190; vol. 75 (1953) 2986.

*Primary Examiner*—Frederick E. Waddell
*Attorney, Agent, or Firm*—Sughrue, Rothwell, Mion, Zinn and Macpeak

[57] ABSTRACT

A method for treating diabetes comprising administering a therapeutically effective amount of a 2-(2,2-disubstituted)ethylimidazoline of the general formula (I)

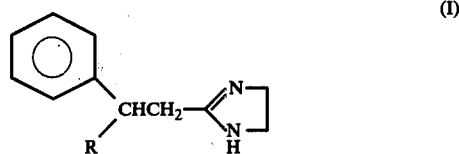

(I)

wherein R is a phenyl group or a 2-pyridyl group or the pharmaceutically acceptable acid addition salts thereof, to a patient having diabetes.

1 Claim, No Drawings

METHOD FOR TREATING DIABETES

BACKGROUND OF THE INVENTION

1. Field of the Invention

This invention relates to a method of treating diabetes using a 2-(2,2-disubstituted)ethylimidazoline of the general formula (I)

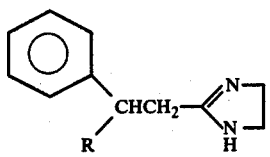

wherein R is a phenyl group or a 2-pyridyl group or the pharmaceutically acceptable acid addition salts thereof.

2. Description of the Prior Art

The compounds of the formula (I) above wherein R is a phenyl group and R is a 2-pyridyl group are known compounds and are described in *Journal of the Chemical Society*, 1950, page 188 and *Journal of the Chemical Society*, Vol. 75, page 2986, (1953), respectively, however the literature only describes the method of synthesizing these compounds of the formula (I) and their antihistaminic activity. These literature references are the only known references which describe the compounds of the general formula (I).

SUMMARY OF THE INVENTION

Examinations have been made in detail on the pharmacological activities of the compounds of the general formula (I), and it has now been unexpectedly discovered that the compounds of the general formula (I) have blood sugar lowering activity. The present invention is based on this discovery.

Accordingly, based on the discovery of the unexpected pharmacological activities of the compounds of the general formula (I), this invention provides a method of treating diabetes which comprises administering a therapeutically effective amount of a 2-(2,2-disubstituted)ethylimidazoline of the general formula (I)

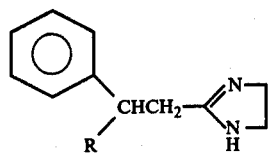

wherein R is a phenyl group or a 2-pyridyl group or the pharmaceutically acceptable acid addition salts thereof to a patient having diabetes.

DETAILED DESCRIPTION OF THE INVENTION

Suitable examples of pharmaceutically acceptable acid addition salts include an inorganic acid salt such as hydrochloric acid salt, hydrobromic acid salt, etc., an organic acid salt such as maleic acid salt, fumaric acid salt, etc.

That the compounds of the general formula (I) are an excellent treatment for diabetes has been found by examining the following pharmacological activities in comparison with heretofore known representative treatments for diabetes utilizing tolbutamide and phenformin.

(i) Blood sugar lowering activity

The compounds of the present invention were orally administered to normal rats, mice, dogs and hereditary diabetic mice(AYKK-mice), and the blood sugar lowering activity was examined. All compounds of the present invention showed superior activities to that of tolbutamide in blood sugar lowering activity. The compounds of the present invention showed excellent effectiveness particularly on AYKK-mice which are considered as a kind of diseased animal, notwithstanding the fact that tolbutamide was uneffective on this type of mice (See Example 1).

(2) Glucose tolerance improving activity

In diabetes a state is observed where glucose utilization is impaired and the elevated blood sugar level caused by glucose load does not drop readily, due to the glucose metabolism abnormality, that is, a state where the glucose tolerance drops. One index for the treatment of diabetes is to improve this glucose tolerance. The compound of the present invention was orally administered to normal rats, Streptozotocin-induced mildly diabetic rats and AYKK-mice, and thereafter glucose was administered intraperitoneally 1 hour later, and the glucose tolerance was examined. The compounds of the present invention showed superior effects to tolbutamide (See Example 2). Further, a lowering of blood sugar in the glucose tolerance test using normal rats was examined with the passage of time, and the results obtained are given in Table 1 below.

Table 1

| | Glucose Tolerance Test in Normal Rats | | | | | | | | |
|---|---|---|---|---|---|---|---|---|---|
| Compound | No. of Animals | Dosage (mg/kg) | Glucose Load (g/kg) | Before Administration (−60 min.) | Blood Glucose Level (mg/dl) | | | | |
| | | | | | 0 | 15 | 30 | 60 | 90 min |
| Tolbutamide | 5 | 20 | 2 | 80 ± 2 | 79±2 | 121±5 | 114±5 | 98±5 | 90±4 |
| Compound A | 5 | 10 | 2 | 84 ± 1 | 72±3 | 83±6 | 87±4 | 76±3 | 68±4 |
| Compound B | 5 | 10 | 2 | 90 ± 2 | 74±3 | 91±9 | 91±5 | 79±4 | 68±5 |
| Control (no Compound administered) | 5 | — | 2 | 87 ± 2 | 84±5 | 132±10 | 134±10 | 116±10 | 115±7 |

*1Compound A = 2-(2,2-diphenyl)ethylimidazoline, and so forth
*2Compound B = 2-[2-phenyl-2-(2-pyridyl)]ethylimidazoline As can be understood from the results in Table 1, Compounds A and B cause scarcely any rise in blood sugar level due to the glucose load, with a dosage which generally significantly lowers the blood sugar level of a fasted normal rat, that is, with a generally employed dosage, in other words, without administering a particularly large amount, and maintains the blood sugar level in the range of the fasting blood sugar level. This prove that Compounds A and B have excellent action in improving glucose tolerance.

(3) Insulin releasing action

The insulin releasing action which is the main cause inducing blood sugar lowering activity is examined in comparison with tolbutamide using normally fed rats and mice, and the compounds of the present invention have been found to have stronger insulin releasing action than tolbutamide. Further, the compounds of the present invention showed an excellent action on insulin releasing action with a low dosage particularly in mice, in spite of the fact that tolbutamide showed little action on insulin release (See Example 3).

(4) Influence on serum lactate level

The biguanide drugs heretofore used as a treatment for diabetes are said undesirably to cause acidosis due to an increase of serum lactate level when such drugs are repeatedly administered. The compounds of the present invention were repeatedly administered for 4 days to normal rats and the serum lactate level was determined every day to compare such with the administration of phenformine which is one example of a biguanide drug. The fact that phenformine gives rise to a remarkable increase in serum lactate level, whereas the compounds of the present invention do not at all give rise to an increase in serum lactate level, proves that the compounds of the present invention are particularly excellent remedies for diabetes (See Example 4).

(5) Blood platelet aggregation inhibiting activity

It is generally said that blood platelet aggregability is accelerated in a diabetes patient and that this secondarily causes blood vessel disorders. The compounds of the present invention inhibit blood platelet aggregation which is induced by collagen in vitro in rat platelet rich plasma. Thus, based on this the compounds of the present invention are expected to be useful in preventing and improving the secondary vasular lesions of diabetes mellitus.

(6) Acute toxicity

As shown in Example 5, the acute toxicity of the compounds of the present invention is relatively low.

As is apparent from the above results, the compounds of the present invention have various excellent properties required for treating diabetes as well as excellent hypoglycemic activities. Accordingly, the compounds of the present invention are extremely excellent for use in treating patients affected with diabetes.

The method for treating diabetes of the present invention comprises administering, generally orally, to a subject having diabetes of a therapeutic amount of the compound of the general formula (I) above. In general, a suitable dosage to an adult is preferably in the range of about 2 to about 10 mg/kg/day. In orally administering the compounds of the invention as a treatment for diabetes the compounds can be administered in the form of tablets, capsules, or granules in a known manner, and these formulations can generally contain suitable pharmaceutically well known and acceptable binders, excipients and disintegration agents.

The unexpected effects of the compounds of the present invention are demmonstrated by the pharmacological tests illustrated in the following Examples. Unless otherwise indicated, all parts, percents, ratios and the like are by weight.

Formulation

Tablet A 1,000 Tablets were prepared according to the following recipe.

| | |
|---|---|
| 2-(2,2-Diphenyl)ethyl-2-imidazoline | 25.0 g |
| Lactose | 200 g |
| Corn Starch | 100 g |
| Magnesium Stearate | 2.5 g |

The active ingredient, i.e., 2-(2,2-diphenyl)ethyl-2-imidazoline, was pulverized to powders of a particle size of 40 mesh and the resulting powder was mixed with other ingredients followed by compressing to prepare tablets.

Tablet B 1,000 Tablets were prepared according to the following recipe.

| | |
|---|---|
| 2-[2-Phenyl-2-(2-pyridyl)]ethyl-2-imidazoline | 25.0 g |
| Lactose | 200 g |
| Corn Starch | 100 g |
| Magnesium Stearate | 2.5 g |

The active ingredient, i.e., 2-[2-phenyl-2-(2-pyridyl)]-ethyl-2-imidazoline, was pulverized to powders of a particle size of 40 mesh, which were then mixed with other ingredients, followed by compressing to obtain tablets.

Suitable dosage of Tablets A and B above is 3 times a day, each time being in an amount of 2 to 5 tablets.

EXAMPLE 1

Test animals which were used included animals which had been fasted for 24 hours to achieve an empty stomach, and animals which had been fed to achieve a full stomach without any restriction of diet. A sample aqueous solution or suspension was orally administered, and blood was sampled with the passage of time from the tail vein or the cephalic vein in order to determine the level of blood sugar by the glucose-oxidase method. Table 2 shows the kind of animal tested, sample tested, numbers of animals, dosage and the blood sugar levels after 1, 2, 3 and 5 hours.

Table 2

| Kind of Animal and Sample | No. of Animals | Dosage (mg/kg PO) | Blood Sugar Level (%) *1 | | | |
|---|---|---|---|---|---|---|
| | | | 1 | 2 | 3 | 5 Hrs. |
| Fasted Rat | | | | | | |
| Tolubutamide | 5 | 10 | 96 | 89 | 92 | 91 |
| | 5 | 25 | 90 | 80 | 76 | 82 |
| Compound A | 5 | 10 | 76 | 71 | 71 | 65 |
| | 5 | 25 | 72 | 67 | 57 | 67 |
| Compound B | 5 | 10 | 71 | 67 | 58 | 73 |
| | 5 | 25 | 83 | 68 | 68 | 76 |
| Fed Mouse | | | | | | |
| Tolbutamide | 5 | 50 | 95 | 92 | 74 | 96 |
| Compound A | 5 | 25 | 54 | 67 | 65 | 76 |
| Compound B | 5 | 25 | 77 | 68 | 78 | 86 |
| Fasted Beagle | | | | | | |
| Compound A | 4 | 25 | 70 | 66 | 64 | — |
| Compound B | 3 | 25 | 76 | 58 | 70 | 71 |
| Fed AγKK Mouse | | | | | | |
| Tolbutamide | 6 | 50 | 94 | 86 | 86 | 92 |
| Compound A | 6 | 10 | 72 | 71 | 62 | 63 |
| | 8 | 25 | 44 | 46 | 41 | 49 |

Table 2-continued

| | Blood Sugar Lowering Activity | | | | | |
|---|---|---|---|---|---|---|
| Kind of Animal and Sample | No. of Animals | Dosage (mg/kg PO) | Blood Sugar Level (%) *1 | | | |
| | | | 1 | 2 | 3 | 5 Hrs. |
| Compound B | 8 | 25 | 77 | 75 | 72 | 78 |

*1Representing the blood sugar level when the blood sugar level of the control to which a sample had not been administered was made 100.

EXAMPLE 2

Glucose Tolerance Improving Activity

A sample aqueous solution or suspension was orally administered to the test animals which had been fasted for 24 hours and one hour later glucose was intraperitoneally or subcutaneously administered to the test animals. Thereafter, blood was sampled from the tail vein with the passage of time in order to determine the blood sugar level by the glucose-oxidase method. Table 3 shows the results, that is, the kind of test animal, number of animals, dosage and the glucose tolerance improving activity which was expressed as a percentage of the sum of blood sugar increments at 4 points a 90 minute period after the administration of the glucose (15, 30, 60 and 90 minutes) to the sum of blood sugar increments at 4 points in the group to which no sample had been administered.

Table 3

| | | | | Glucose Tolerance Test | | |
|---|---|---|---|---|---|---|
| Kind of Animal | No. of Animals | Dosage (mg/kg,) PO) | Glucose Load (g/kg) | Glucose Tolerance Improving Activity (%) *3 | | |
| | | | | Tolbut-amide | Cpd. A | Cpd. B |
| Normal Rat | 5 | 10 | 2 | 64.5 *2 | 15.7 | 22.0 |
| Streptozotocin Mild Diabetes Rat *4 | 5 | 10 | 1 | 67.4 *2 | 25.2 | — |
| aykk*5 Mouse | 5 | 25 | 1 | 69.6 *1 | 52.5 | 62.7 |

*1Tolbutamide dosage 50 mg/kg.
*2Tolbutamide dosage 20 mg/kg.
*3The glucose tolerance improving activity means the percentage of the sum of the blood sugar increments due to the glucose load at 4 points, 15, 30, 60 and 90 minutes (blood sugar increments meaning the difference in blood sugar level between pre- and post-glucose load) in the group given the sample to the sum of the blood sugar increments due to the glucose load at 4 points in the control group to which no sample had been administered; the value 100 representing no improvement in the glucose tolerance was at all observed, and the value 0 representing no influence due to the glucose load was observed due to the pre-administration of the sample.
*4The streptozotocin-induced mildly diabetic rats were produced by injecting a streptozotocin solution in saline adjusted to pH 4.5 with 0.05 M citric acid (at a dose of 20mg/2 ml/kg) into the tail vein of 8 week old male rats of the Wistar strain which had been fasted for 24 hours. 48 Hours after the injection all rats showed a blood sugar level as high as above 350 mg/dl, and thereafter the blood sugar level gradually returned to normal. Although these animals keep the fasting blood sugar level to 90–100 mg/dl and the fed blood sugar level to 130–180 mg/dl, they show apparently an impaired glucose tolerance and show symptoms of mild diabetes.
*5AYKK-mouse was obtained by mating a yellow mouse having symptoms of hereditary obesity and hyperglycemia with a KK-mouse suffering from a hereditary diabetes characterized by glucose tolerance abnormality (Iwatsuka, et al, Endocrinologica Japonica Vol. 17 (1970), pp 23) is characterized by decrease in glucose tolerance, abnormal secretion of insulin, continuous hyperglycemia, glucosurea, obesity and renal glomerular lesions and therefore is a genetically diabetic animal model resembling human adult onset diabetes. The test animals used hereinafter in the various tests of the present invention are those which show a fed blood sugar level of 400–500 mg/dl, which are strongly positive in urine sugar and which are 12–20 weeks old after birth.

EXAMPLE 3

Insulin releasing action

Among the test animals fed rats were anesthetized by administration of pentobarbital (40 mg/kg, ip), and administered, intravenously with an isotonic sodium chloride solution of Compound A. An aqueous solution of the sample was orally administered to fed mice. In both cases blood was sampled from the tail vein with the passage of time, and the blood insulin was determined by the radioimmunoassay method of Morgen et al [Diabetes, Vol. 12, pp 115 (1963)]. At the same time blood sugar was also determined. Table 4 shows the results, that is, test animals, samples, number of animals, dosage, amount of insulin released after administration of the sample, and blood sugar. The amount of insulin released in Table 4 was obtained by determining the difference between the blood insulin level at 5 points (5, 10, 20, 30, 40 minutes) during a 40 minute period after administration of the sample in the case of rats or 3 points (0.5, 1.0, 2.0 hours) during a 2 hour period after administration of the sample in the case of mice and the blood insulin level at 0 minute just before administration of the sample and then by summing up these differences.

Table 4

| | | Insulin Releasing Action | | | |
|---|---|---|---|---|---|
| Kind of Animal | No. of Animals | Dosage (mg/kg) | Manner of Administration | Amount of Insulin Released (μunit/ml) | Blood Sugar Level (%) |
| Fed Rats | | | | | |
| Non-treated Control Group | 6 | — | — | 50±8 | — |
| Tolbutamide | 6 | 50 | iv | 189±26 | 56 *1 |
| Compound A | 6 | 25 | iv | 250±15 | 62 *1 |
| Fed Mice | | | | | |
| Non-treated Control Group | 5 | — | — | 0±3.7 | — |
| Tolbutamide | 5 | 50 | po | −2.2±3.3 | 95.7 *2 |

Table 4-continued

| Kind of Animal | Insulin Releasing Action | | | | Blood Sugar Level (%) |
|---|---|---|---|---|---|
| | No. of Animals | Dosage (mg/kg) | Manner of Administration | Amount of Insulin Released (μunit/ml) | |
| Compound A | 5 | 25 | po | 57±14.2 | 69.8 *2 |

*1 Blood sugar after 90 minutes when the blood sugar level in the control group was made 100.
*2 Blood sugar level after 2 hours when the blood sugar level in the control group was made 100.

EXAMPLE 4

Influence on serum lactate level

Compound A was repeatedly administered for 4 days to normal rats in a dosage of 200 mg/kg/day, and blood was sampled with the passage of time in order to determine the serum lactate level. Table 5 shows the results, that is, the sample, number of animals and the serum lactate level.

Table 5

| | Influence on Serum Lactate Level | | | |
|---|---|---|---|---|
| Sample | No. of Animals | *1 Serum Lactate Level (μ mol/ml) | | |
| | | 0 Day | After 1 Day | After 4 Days |
| Phenformin | 5 | 1.061±0.099 | 2.086±0.066 | 3.009±0.641 |
| Compound A | 5 | 0.993±0.051 | 1.386±0.073 | 1.125±0.113 |

*1 Serum lactate level in the normal rate was 1.125 μ mole/ml (95% confidence limit 0.961 - 1.287).

EXAMPLE 5

Blood platelet aggregation inhibiting activity

Citrated rat blood was centrifuged in order to obtain platelet rich plasma, and to 0.4 ml of this plasma was added 50 μl of sample solution. To the resulting solution was added 50 μl of collagen suspension under stirring, and platelet aggregation reaction was determined according to the method of Born [*Nature*, Vol. 194, pp. 927 (1962)]. The concentration of the sample ($ID_{50}$) which inhibits 50% of the aggregation reaction of the control without the test sample added is shown in Table 6 below.

Table 6

| | Blood Platelet Aggregation Inhibition | |
|---|---|---|
| | Activity and Acute Toxicity (rat) | |
| Sample | Platelet Aggregation Inhibition Activity, $ID_{50}$ (μM) | Acute Toxicity (rat) $ID_{50}$ (mg/kg) |
| Compound A | 70 | 562 |
| Compound B | 300 | 867 |

While the invention has been described in detail and with reference to specific embodiments thereof, it will be apparent to one skilled in the art that various changes and modifications can be made therein without departing from the spirit and scope thereof.

What is claimed is:

1. A method for treating diabetes comprising administering a therapeutically effective amount of 2-[2-phenyl-2-(2-pyridyl)]ethylimidazoline to a patient having diabetes.

* * * * *